United States Patent
Wolter et al.

(10) Patent No.: US 8,926,674 B2
(45) Date of Patent: Jan. 6, 2015

(54) FIXATION SYSTEM FOR BONES WITH A SENSOR AND TELEMETRY SYSTEM

(75) Inventors: Dietmar Wolter, Hoisdorf (DE); Felix Capanni, Neu-Ulm (DE)

(73) Assignee: Dietmar Wolter, Hoisdorf (DE)

( * ) Notice: Subject to any disclaimer, the term of this patent is extended or adjusted under 35 U.S.C. 154(b) by 1361 days.

(21) Appl. No.: 12/278,346

(22) PCT Filed: Jan. 30, 2007

(86) PCT No.: PCT/EP2007/000794
§ 371 (c)(1),
(2), (4) Date: Nov. 21, 2008

(87) PCT Pub. No.: WO2007/090543
PCT Pub. Date: Aug. 16, 2007

(65) Prior Publication Data
US 2009/0222050 A1    Sep. 3, 2009

(30) Foreign Application Priority Data
Feb. 7, 2006   (DE) .......................... 10 2006 006 341

(51) Int. Cl.
A61B 17/80   (2006.01)
A61B 5/00    (2006.01)
A61B 17/60   (2006.01)
A61B 17/72   (2006.01)
A61B 19/00   (2006.01)
A61B 17/00   (2006.01)

(52) U.S. Cl.
CPC ............... *A61B 17/80* (2013.01); *A61B 5/0031* (2013.01); *A61B 2019/464* (2013.01); *A61B 17/60* (2013.01); *A61B 2017/00734* (2013.01); *A61B 17/72* (2013.01); *A61B 5/4504* (2013.01); *A61B 2562/0261* (2013.01)
USPC .............................. 606/286; 606/60; 600/587

(58) Field of Classification Search
USPC ........ 606/70–71, 280–299; 623/17.11–17.19; 600/587
See application file for complete search history.

(56) References Cited

U.S. PATENT DOCUMENTS 4,794,918 A * 1/1989 Wolter .......................... 606/295
5,425,775 A * 6/1995 Kovacevic et al. ............. 128/898

(Continued)

FOREIGN PATENT DOCUMENTS

AT   386117   12/1987
DE   43 43 117 A1   6/1995

(Continued)

OTHER PUBLICATIONS

Machine Translation of WO 2005/074821. Accessed on EPO website Jun. 6, 2012.*

*Primary Examiner* — Edward Moran
(74) *Attorney, Agent, or Firm* — Alix, Yale & Ristas, LLP

(57) ABSTRACT

Fixation system for bones with a connection support, at least one bone screw that can be inserted into a through hole of the connection support and a sensor and telemetry system, wherein the sensor and telemetry system is arranged on a separate plate, which can be connected with the connection support.

25 Claims, 3 Drawing Sheets

(56) References Cited

U.S. PATENT DOCUMENTS

| | | | |
|---|---|---|---|
| 6,034,296 A | 3/2000 | Elvin et al. | |
| 6,289,238 B1 * | 9/2001 | Besson et al. | 600/509 |
| 7,708,777 B2 * | 5/2010 | O'Neil et al. | 623/17.14 |
| 8,343,153 B2 | 1/2013 | Duda et al. | |
| 2004/0015211 A1 * | 1/2004 | Nurmikko et al. | 607/61 |
| 2005/0010300 A1 * | 1/2005 | Disilvestro et al. | 623/18.12 |
| 2005/0165485 A1 * | 7/2005 | Trieu | 623/17.13 |
| 2008/0154265 A1 * | 6/2008 | Duda et al. | 606/70 |

FOREIGN PATENT DOCUMENTS

| | | |
|---|---|---|
| DE | 4343117 A1 | 6/1995 |
| DE | 19711628 A1 | 7/1998 |
| DE | 198 58 889 A1 | 6/2000 |
| WO | 00/33752 A1 | 6/2000 |
| WO | 2004024012 A1 | 3/2004 |
| WO | 2005074821 A2 | 8/2005 |
| WO | WO2005074821 * | 8/2005 |

* cited by examiner

FIXATION SYSTEM FOR BONES WITH A SENSOR AND TELEMETRY SYSTEM

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The invention relates to a fixation system for bones with a sensor and telemetry system.

Fixation systems are used in osteosynthesis, wherein the connection support bridges the fracture and is connected with the bone fragments via at least one bone screw. The connection support is for example a bone plate, a marrow nail or external fixation. It is thereby advantageous if the bone screw in the connection support is blocked in a permanently angle-stable manner.

Particularly advantageous is the selectability of the screw direction before the permanently angle-stable blocking of the bone screw in the connection support. The angle-stable connection of bone screw and connection support leads to a stability increase for the entire assembly trough the special type of transfer of forces and loads. This transfer is characterized by the area-wise force distribution. Furthermore, biomechanical and clinical results indicate better healing processes.

The check of the healing processes during osteosynthesis is possible through so-called imaging procedures. Above all, this concerns X-ray examinations, magnetic resonance imaging and computer tomography. It is known that the informational value of these imaging procedures lags several weeks behind that of the actual healing process.

It is required to safely assess the ability of the healing tissue with respect to the transfer of forces in order to be able to close on the status of the healing process, to be able better conduct aftercare and to identify early on potential defective healings.

Fixation systems for bones were already combined with sensor systems earlier. Resistance strain gauges were hereby used, which were connected with cables, which were led through the skin to the outside. The problem of infections in particular caused these types of systems to only be used in exceptional cases.

For several years, sensor systems that work together with a telemetry system, which transmits the measurement values obtained from the sensor system in the body to the outside wirelessly, have been used in clinical applications The production of these systems is difficult, complicated and cost-intensive. Thus, these systems have only been used in individual cases—e.g. in the area of the spinal column or the hip joint—in order to answer questions regarding the load tolerance, the forces and after healing. Sensor and telemetry systems are connected with the fixation system through adherence.

Based on the fixed connection of fixation, sensor and telemetry system, the operator must make a decision early enough about whether the patient needs this combined system.

Only at the end of the operation, after the bone fixation is complete, is an assessment possible with respect to the future healing process. Many important factors for the healing are impacted by the operative progression.

U.S. Pat. No. 6,034,296 and WO-A-2005074821 disclose fixation systems for bones with a connection support, at least one bone screw that can be inserted into a through hole of the connection support and a sensor and telemetry system, which is arranged on a separate plate, which can be connected with the connection support.

Based on this assumption, the object of the invention is to create a fixation system for bones with a sensor and telemetry system, in which the force flow takes place via the sensor system.

BRIEF SUMMARY OF THE INVENTION

The fixation system for bones has a connection support, at least one bone screw that can be inserted into a through hole of the connection support and a sensor and telemetry system, characterized in that the sensor and telemetry system is arranged on a separate plate, which can be connected with the connection support. The connection support and separate plate have devices for the formation of at least one groove/tongue connection between the connection support and the plate.

Due to the fact that in the fixation system according to the invention the sensor and telemetry system is arranged on a separate plate, which can be connected with the connection support, the operator can decide at the end of the operation whether the fixation system must be equipped with the sensor and telemetry system. If it is not required, the sensor and telemetry system is omitted and only the fixation system is used. This saves time and money. It is easier for the operator to decide on the use of this combined system. However, if the patient needs the combined system, then the operator can simply connect the plate with the sensor and telemetry system to the fixation system.

The invention can be used in particular for fixation systems, in which at least one bone screw has a permanently angle-stable connection with the support. It can for example be used for fixation systems, in which at least one bone screw sits in a defined angle alignment in the through hole. The through hole can thereby guide the bone screw in a defined angle alignment or be realized with a specified thread, into which the bone screw can only be screwed in a defined alignment.

In accordance with a preferred embodiment, the bone screw and through hole have devices for the angle-stable connection in a selectable angle alignment. In accordance with one embodiment, these devices are devices for the shaping of a thread between the bone screw and the through hole. This makes it possible to also connect in a permanently angle-stable manner a bone screw that can be inserted in variable angle alignments into the connection support with the connection support.

The devices for the forming of a thread comprise e.g. a thread on the bone screw and a threadless through hole, into which the bone screw can be screwed under a selectable angle under formation of an inner thread. According to one embodiment, the materials of the bone screw and the inner wall of the through hole or the connection support hereby have different hardness levels. For example, pure titanium is used for the bone screw and a titanium alloy for the connection support or vice versa. Other potential embodiments of the invention for the forming of a thread are described in DE 43 43 117 C2, the entire contents of which is incorporated herein by reference.

The invention enables the use of different sensor systems. The sensor system measures for example chemical parameters or the temperature or the forces straining the fixation system or the deforming of the fixation system. In accordance with one embodiment, the sensor system comprises a resistance strain gauge (RSG). The expansion of the connection support can be captures using the RSG, from which in turn the forces straining the connection support can be determined.

According to one embodiment, in particular when the sensor system comprises a sensor for measuring the deformations or forces, the sensor system is mounted on a separate plate and the separate plate on the connection support such that the force flow takes place over the connection support and over the sensor system so that the deformations or forces decreasing during the healing process are measured and telemetrically transmitted.

According to one embodiment, the sensor system for measuring the deformations or forces is permanently connected with the separate plate. According to one embodiment, the separate plate has devices for the form- and/or force- and/or integral joint connection of connection supports and plate. According to one embodiment, the devices for the connection are arranged on different sides of the sensor system so that the force flow takes place between the devices for the connection via the sensor system. It is achieved through the deep connection of separate plate and connection support that a strain of the connection support of corresponding force flow takes place via the sensor system.

The groove/tongue connection enables in particular a form-fit connection between connection support and plate. Moreover, a force-fit connection is possible, in that the spring is pressed into the groove. This can also lead to a integral joint connection, in particular if through the combination of suitable materials for spring and groove a welding takes place when the spring is pressed into the groove. This is for example the case in the case of a titanium alloy for the spring and of pure titanium for the groove or vice versa, since the materials have different levels of hardness.

In accordance with one embodiment, the connection support and the separate plate have devices for the formation of at least one groove/tongue connection between the connection support and the plate. The groove/tongue connection enables in particular a form-fit connection between the connection support and the plate. Moreover, a force-fit connection is possible in that the spring is pressed into the groove. This can also lead to a integral joint connection, in particular if through the combination of suitable materials for spring and groove a welding takes place when the spring is pressed into the groove. This is for example the case in the case of a titanium alloy for the spring and of pure titanium for the groove or vice versa, since the materials have different degrees of hardness.

In accordance with one embodiment, the connection support has at least one groove and the plate at least one spring complementary to the groove for insertion into the groove. In accordance with one embodiment, several groove/tongue connections are arranged on different sides of the sensor system so that the force fit takes place via the sensor system. In accordance with another embodiment, the groove is circular or ovular and the spring is shaped complementarily to the groove and the sensor system is arranged within the closed curve defined by the groove/tongue connection. This single groove/tongue connection also leads to a force flow through the sensor system. In accordance with one embodiment, the plate is also circular or ovular, wherein the shape of the plate preferably corresponds with the groove/tongue connection.

In accordance with another embodiment, the groove and the spring are conical. In accordance with one embodiment, the groove narrows to its base and/or the spring narrows to its free end. This makes it possible to press the spring into the groove under the gradual introduction of force and to hereby establish a particularly deep connection between the plate and the connection support.

In accordance with one embodiment, the plate is made out of a harder material than the connection support or vice versa so that a particularly deep connection is established between the plate and the connection support through the material deformation during the creation of the groove/tongue connection. This ensures that the transfer of forces takes place in a permanent and even manner.

It is possible to connect the plate and connection support together just through a groove/tongue connection. The groove/tongue connection is e.g. designed as a snap connection or additional snap elements to snap the plate and the connection support together are added to the snap connection. In accordance with one embodiment, at least one screw connection is present for connecting the plate and connection support. The screw connection is e.g. present between the circumference of a circular spring and a circular groove. In accordance with one embodiment, the screw connection comprises a screw, which can be screwed through a through hole of the plate into a threaded bore hole of the connection support. In accordance with another embodiment, the plate can be connected to the connection support by means of at least two diametrically opposed screw connections. This is for example advantageous in the case of a circular or ovular groove/tongue connection between plate and connection support or a correspondingly shaped plate.

It is also possible to produce the so-called separate plate as a screw with external threads, which is partial hollow on the inside, in order to receive the resistance strain gauge and the necessary electronics.

In accordance with other embodiments, the connection is achieved between the sensor system and the plate and/or the plate and the connection support through clamping, fixation or other means. Furthermore, the invention relates to designs, in which different types of connections are combined.

In accordance with one embodiment, the sensor and/or telemetry system is at least partially arranged below the plate in an area surrounded by the groove/tongue or the screw connection. In the case of this arrangement, the sensor and/or telemetry system is at least partially encapsulated between the connection support and the plate. In accordance with one embodiment, the sensor and/or telemetry system is at least partially arranged in a capsule arranged on the top side of the plate.

In accordance with a further embodiment, the capsule is made of metal (e.g. of titanium) and/or plastic. It is possible to achieve the encapsulation through a metal foil. In order to ensure that the signal makes its way to the outside, the metal capsule has a window according to another embodiment, through which the telemetry signal can be transmitted to the outside.

In accordance with one embodiment, the sensor and telemetry system has an antenna. The antenna enables a wireless transmission of the signals to the outside. In order to facilitate the wireless transmission of the signal to the outside, it can be advantageous to connect the sensor unit with an antenna, the end of which reaches under the skin. The partial absorption of the signal can thus be avoided through the soft shell.

In accordance with one embodiment, a memory and telemetry unit that can be placed under the skin is present with a receiver antenna that can be placed in the vicinity of the sensor and telemetry system. It is hereby possible to keep smaller the part of the sensor and telemetry system that is arranged on the fixation system. This simplifies the data transfer and facilitates the energy transport. In accordance with another embodiment, the sensor and telemetry system has an antenna for the wireless transmission of signals to the receiver antenna.

In accordance with one embodiment, the sensor and telemetry system and/or the memory and telemetry system has a power supply through induction and/or through at least one battery system and/or through at least one rechargeable battery system. It is possible through induction to get energy needed to conduct measurements from the outside. A charging of capacitors and/or batteries and/or rechargeable batteries can hereby take place.

The signals received by the sensor and telemetry unit can be collected in an external data memory, which communicates with the known data transmission systems and/or data processing systems.

The sensor and telemetry system that can be mounted on a fixation system for bones during the operation at the best point in time permits a continuous data capture and a wireless data transmission using conventional memory technologies. The system takes into account economic aspects and permits use when indication is proven.

BRIEF DESCRIPTION OF THE SEVERAL
VIEWS OF THE DRAWINGS

Other uniquenesses and advantages of the invention result from the below description of the subsequent drawings of exemplary embodiments. The drawings show the following:

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated In the below explanation of various exemplary embodiments, corresponding components are labelled with the same reference numbers.

Figure 1:
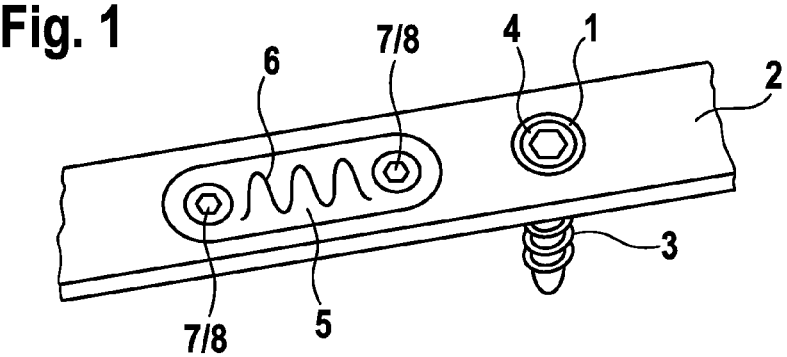
FIG. 1 shows a roughly schematic perspective view of a fixation system with sensor and telemetry system on a plate and multi-directional blockable bone screw.

In accordance with FIG. 1, a multi-directional, blockable bone screw 3 in the form of a bone plate is used in a through hole 1 of a connection support 2. The bone screw 3 can be screwed with a bone, wherein a thread is molded into the connection support 2 by a thread in the vicinity of the screw head 4.

Furthermore, a separate plate 5 with a resistance strain gauge 6 is arranged on the connection support 2. The separate plate 5 is connected with the connection support 2 by means of other screws 7, which are screwed into the thread holes 8 of the connection support 2.

Figure 2:
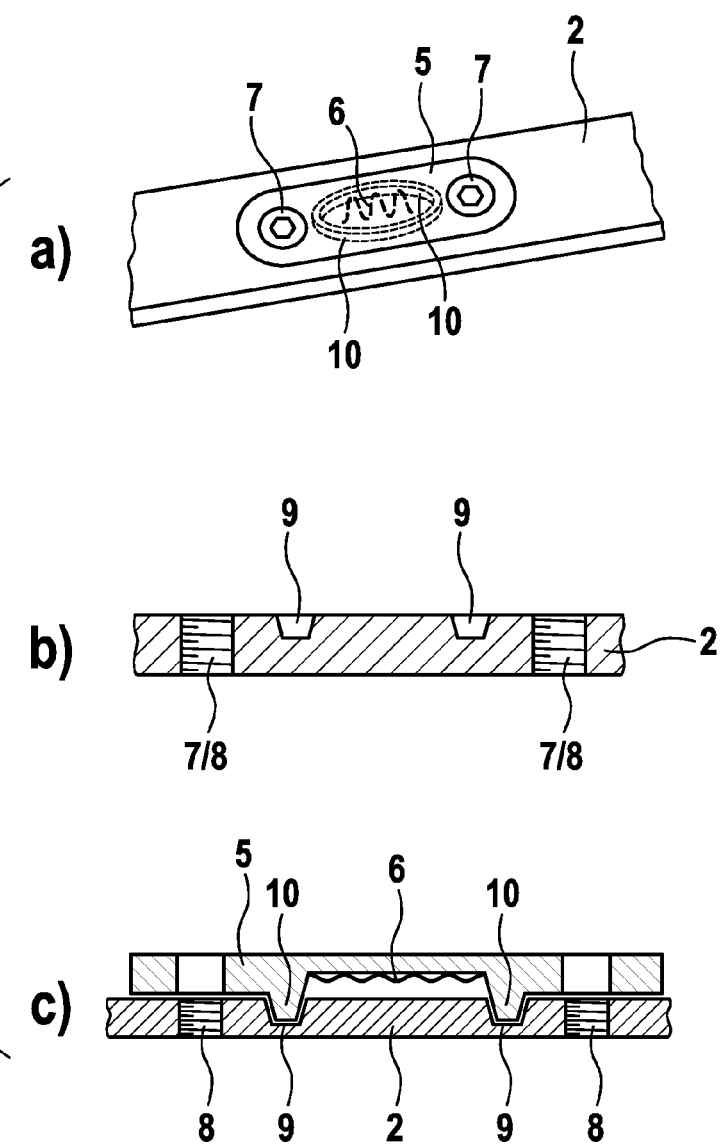
FIG. 2a shows a roughly schematic perspective view of a fixation system with sensor and telemetry system on a plate.
FIG. 2b shows a longitudinal section through the connection support.
FIG. 2c shows a side view.

In accordance with FIG. 2, the connection support 2 has a groove 9 that is ovular when seen from the top and conical when seen from the cross-section, into which a complementary spring 10 engages with a separate plate 5. The separate plate 5 is in turn screwed with the connection support 2 by means of screws 7, which penetrate the holes of the separate plate 5 and engage in thread holes 8 of the connection support 2. This establishes a particularly deep connection between plate 5 and connection support 2 so that the force flow through the area between the groove/tongue connections 9, 10 corresponds with the force flow within the oval groove 9 of the connection support 2.

Figure 3:
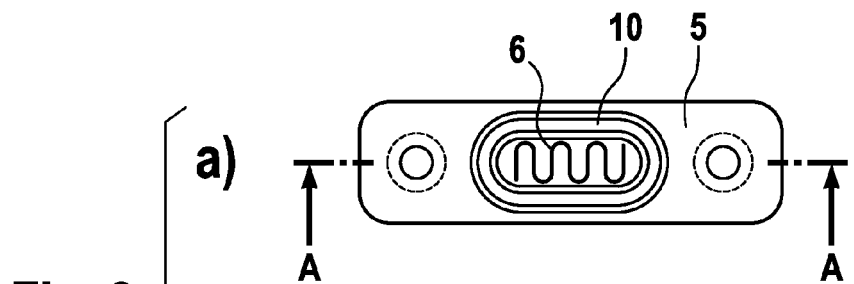
FIG. 3a shows a view from the bottom.
FIG. 3b shows a longitudinal section of a plate for carrying a sensor with an ovular spring.
Figure 4:
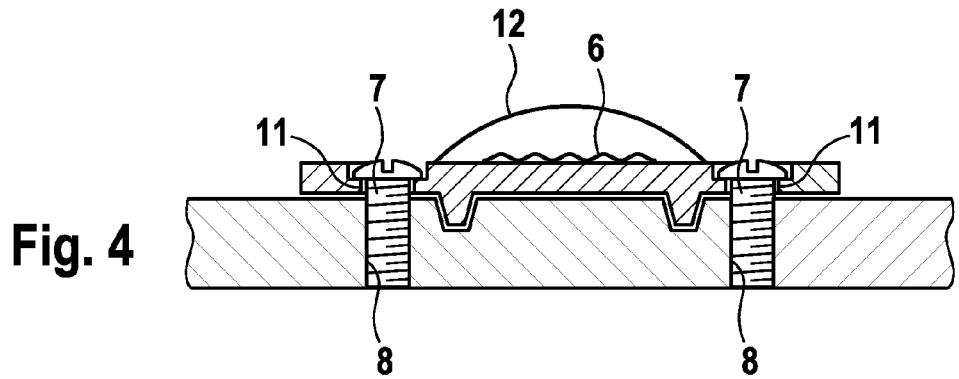
FIG. 4 shows a longitudinal section of a plate in accordance with FIG. 3 screwed with a connection support, which has an encapsulated electronic unit on the top side.

In accordance with FIG. 3, the separate plate 5 has an ovular spring 10 with conical cross-section. The spring 10 can be rolled in a complementary groove 9 of the connection support 2, as shown in FIG. 4. The separate plate 5 is fixed by means of screws 7, which the holes 11 of the separate plate 5 reach through and are screwed into the thread holes 8 of the connection support 2'.

In accordance with FIG. 4, the sensor and telemetry system 6 is arranged within a capsule 12 on the top side of the separate plate 5.

Figure 5:
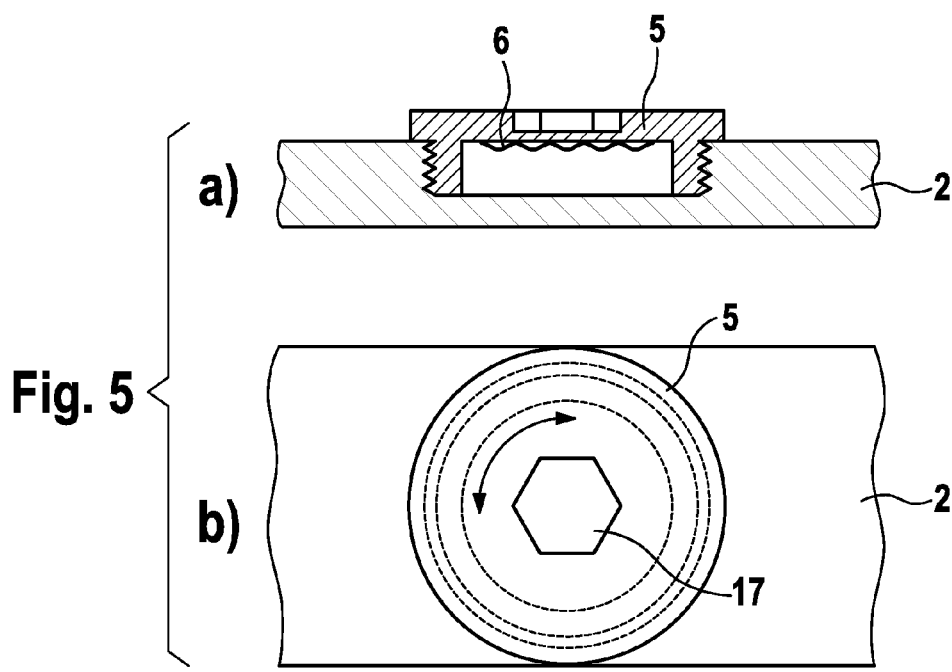
FIG. 5 shows a separate plate as a screwable element, which has the resistance strain gauge on the inside.

In accordance with FIG. 5, the separate plate 5 is created as a flat screw that is partially hollow on the inside 17. It has the sensor and telemetry unit 6 on the inside. The sensor and telemetry system 6 can also be placed on the outside and is in this case surrounding by a capsule 12. The screwing in of this separate screwable plate is facilitated by a hexagonal recess on the outer surface.

Figure 6:
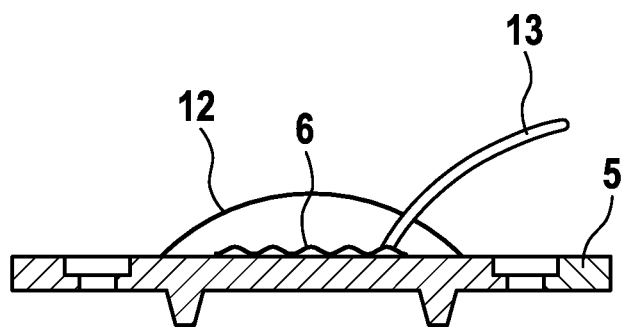
FIG. 6 shows a longitudinal section of a plate with an encapsulated sensor and telemetry system with antenna.

In accordance with FIG. 6, the separate plate 5 has a sensor and telemetry system 6 with a capsule 12, wherein a transmitting antenna 13 is led out of the capsule 12 in order to ensure an easier wireless signal transmission.

Figure 7:
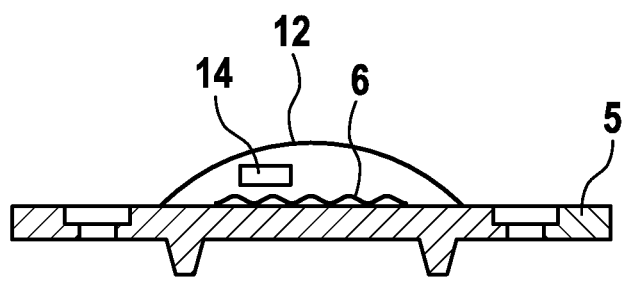
FIG. 7 shows a longitudinal section of a plate with encapsulated sensor and telemetry system in a capsule with window for the signal emission.

In accordance with FIG. 7, the sensor and telemetry system 6 is arranged within a capsule 12 on the separate plate 5. The capsule 12 has a window 14 so that signals of the sensor and telemetry system 6 can get out of the capsule 12.

Figure 8:
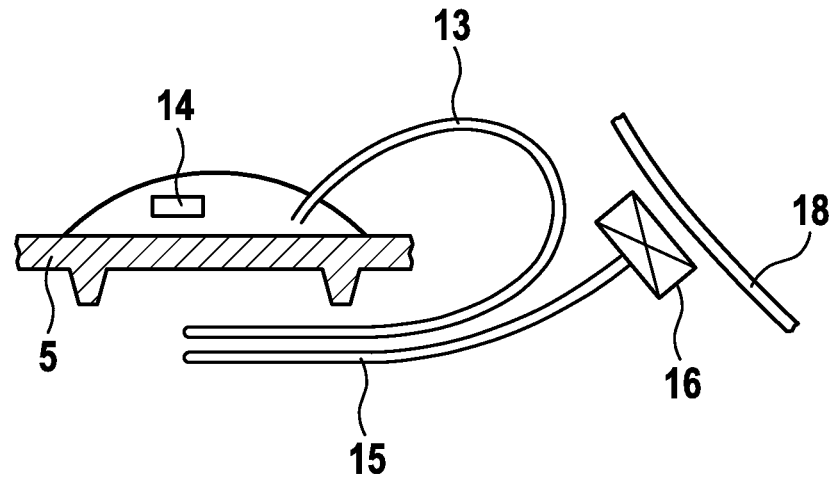
FIG. 8 shows a side view of a plate with sensor and telemetry system in a capsule with window and/or a transmitting antenna for facilitating the signal emission and associated memory and telemetry unit, which is located below the skin.

In accordance with FIG. 8, another memory and telemetry unit 16 lying below the skin with a receiving antenna 15 is attached to the separate plate 5 with the window 14. The memory and telemetry unit 16 is located under the skin 18 and the receiving antenna 15 is arranged near the window 14 so that a wireless signal transfer can take place through the window 14 and/or the transmitting antenna 13 to the receiving antenna 15. Power can be fed to the memory and telemetry unit 16 inductively from the outside or the memory and telemetry unit is provided with a battery, the memory capacity of which is sufficient for the duration of the therapy.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. A fixation system for bones comprising:
   a connection support defining at least one through hole and defining one of a groove or tongue in the shape of a closed curve;
   at least one bone screw for insertion through said through hole to fix said connection support to a bone; and
   a sensor and telemetry assembly arranged on a region of a plate encompassed by the other of a groove or tongue complementary to the shape of said closed curve and including a sensor secured to and supported by said plate within said closed curve,
   wherein said groove comprises an inner surface and an outer surface defining a channel and said tongue comprises a projection that fits between said inner and outer surfaces, and said sensor and telemetry assembly can be secured to said connection support by insertion of said tongue into said groove and forces applied to said connection support are transferred to said plate by the tongue and groove interface between said connection support and said sensor and telemetry assembly when said sensor and telemetry assembly is secured to said connection support.

2. Fixation system according to claim 1, in which the at least one bone screw can be fastened in the through hole.

3. Fixation system according to claim 2, in which the at least one through hole is threaded.

4. Fixation system according to claim 1, in which the sensor comprises a resistance strain gauge.

5. Fixation system according to claim 4, in which the resistance strain gauge is adhered to the plate.

6. Fixation system according to claim 5, in which said plate has opposite first and second sides, said sensor is adhered to one of said first or second sides and the other of said tongue or groove is arranged on the other of said first or second side of said plate.

7. Fixation system according to claim 1, in which the groove is circular or oval and the tongue is formed complementary to the groove.

8. Fixation system according to claim 1, in which the plate is circular or oval.

9. Fixation system according to claim 1, in which the groove and the tongue are conical.

10. Fixation system according to claim 1, in which the groove narrows to its base and/or the tongue narrows to its free end.

11. Fixation system according to claim 1, in which the plate is made of a harder material than the connection support or vice versa.

12. Fixation system according to claim 1, with at least one screw connection for connecting the plate and connection support.

13. Fixation system according to claim 12, in which the screw connection comprises a screw, which can be screwed through a through hole of the plate into a threaded bore hole of the connection support.

14. Fixation system according to claim 12, in which the plate can be connected with the connection support by means of at least two diametrically opposed screw connections.

15. Fixation system according to claim 1, in which the sensor and telemetry assembly is at least partially arranged below the plate in an area surrounded by the groove/tongue connection.

16. Fixation system according to claim 1, in which the sensor and telemetry assembly is at least partially arranged in a capsule arranged on the top side of the plate.

17. Fixation system according to claim 16, in which the capsule is made of metal or plastic.

18. Fixation system according to claim 17, in which a metallic capsule has a window.

19. Fixation system according to claim 1, in which the sensor and telemetry assembly has a transmitting antenna.

20. Fixation system according to claim 19, in which the transmitting antenna can be placed within the subcutaneous tissue.

21. Fixation system according to claim 19, in which the transmitting antenna has a plug-in connection with the sensor and telemetry assembly.

22. Fixation system according to claim 1, which comprises a memory and telemetry unit that can be arranged under the skin with a receiving antenna.

23. Fixation system according to claim 22, in which the sensor and telemetry assembly and/or the memory and telemetry unit has a power supply through induction and/or through at least one battery system and/or through at least one rechargeable battery system and/or at least one capacitor.

24. Fixation system according to claim 1, in which the connection support is a bone plate or a marrow plate.

25. Fixation system according to claim 2, in which the at least one bone screw is threaded.

* * * * *